(12) United States Patent
Bonnell et al.

(10) Patent No.: US 8,038,000 B2
(45) Date of Patent: *Oct. 18, 2011

(54) HYDROGEN PEROXIDE POINT-OF-USE WIPERS

(75) Inventors: Karen F. Bonnell, Montvale, NJ (US); Ram Sivakumar, Edison, NJ (US); Howard D. Siegerman, Hillsdale, NJ (US); Bradley T. Lyon, Winston-Salem, NC (US)

(73) Assignee: Illinois Tool Works Inc., Glenview, IL (US)

( * ) Notice: Subject to any disclaimer, the term of this patent is extended or adjusted under 35 U.S.C. 154(b) by 854 days.

This patent is subject to a terminal disclaimer.

(21) Appl. No.: 11/839,697

(22) Filed: Aug. 16, 2007

(65) Prior Publication Data

US 2009/0044836 A1    Feb. 19, 2009

(51) Int. Cl.
*B65D 69/00* (2006.01)
(52) U.S. Cl. ......... 206/219; 206/223; 206/484; 206/812
(58) Field of Classification Search .................. 206/209, 206/207, 233, 210, 205, 812, 222, 219, 440, 206/223, 221, 581, 484, 220; 383/38
See application file for complete search history.

(56) References Cited

U.S. PATENT DOCUMENTS

| | | | |
|---|---|---|---|
| 2,999,265 A | 9/1961 | Duane et al. | |
| 3,393,796 A | 7/1968 | Clarke | |
| 3,889,804 A * | 6/1975 | Ravich | 206/221 |
| 5,267,646 A | 12/1993 | Inoue et al. | |
| 5,287,961 A | 2/1994 | Herran | |
| 5,616,337 A | 4/1997 | Kasianovitz et al. | |
| 5,988,371 A * | 11/1999 | Paley et al. | 206/229 |
| 6,001,187 A | 12/1999 | Paley et al. | |
| 6,062,381 A | 5/2000 | Paley et al. | |
| 6,082,534 A | 7/2000 | Dotson | |
| 6,827,080 B2 | 12/2004 | Fish et al. | |
| 6,945,402 B1 | 9/2005 | Gueret | |
| 7,357,248 B2 * | 4/2008 | Sivakumar et al. | 206/219 |

(Continued)

FOREIGN PATENT DOCUMENTS

EP    0594449 A    4/1994

(Continued)

OTHER PUBLICATIONS

International Search Report for PCT/US2008/067966 dated Sep. 9, 2009.

*Primary Examiner* — Steven A. Reynolds
(74) *Attorney, Agent, or Firm* — Levenfeld Pearlstein, LLC

(57) ABSTRACT

A hydrogen peroxide point of use wetted wiper system includes a packaging with a first, a second, and a third compartment, wherein the separate compartments are mergable. Wipers are disposed in the third compartment. Disposed in the second compartment is dry urea hydrogen peroxide, isolated from the wipers. Disposed in the first compartment is a solvent, wherein the solvent is isolated from the wipers and the urea hydrogen peroxide. The first and second compartments can merge to form a unified compartment such that the solvent is combined with the urea hydrogen peroxide at a point of use to form liquid 6% hydrogen peroxide solution. The unified compartment then merges with the third compartment such that the liquid hydrogen peroxide wets the wipers. The liquid hydrogen peroxide concentration and amount is proportional to the wiper absorptive capacity, number, size, and degree of desired saturation.

9 Claims, 1 Drawing Sheet

U.S. PATENT DOCUMENTS

| | | | |
|---|---|---|---|
| 2004/0065315 A1 | 4/2004 | Fish et al. | |
| 2006/0124476 A1 | 6/2006 | Sivakumar | |
| 2006/0144737 A1* | 7/2006 | Rein | 206/440 |
| 2006/0168748 A1* | 8/2006 | Dotterman et al. | 15/115 |
| 2007/0134302 A1 | 6/2007 | Koenig | |

FOREIGN PATENT DOCUMENTS

| | | |
|---|---|---|
| WO | WO 93/10019 A | 5/1993 |
| WO | 9426317 | 11/1994 |
| WO | 9524525 | 9/1995 |
| WO | PCT/US2005/031293 | 8/2005 |
| WO | 2006065297 | 6/2006 |

* cited by examiner

HYDROGEN PEROXIDE POINT-OF-USE WIPERS

BACKGROUND OF THE INVENTION

The present invention is directed to an apparatus and method for providing wetted wipers. More particularly, the present invention pertains to a hydrogen peroxide point-of-use wetted wiper system.

Many attempts have been made to provide effective ways to clean areas. One of the most easy and prevalent ways to achieve clean areas is by wiping the surfaces of an area with a cleaning solution and a wipe. The term "cleaning agent" is intended to include disinfectants, sanitizers, antimicrobials, virucides, fungicides, and the like and is intended to encompass the active ingredients and not additives such as detergents, surfactants, stabilizing agents and the like.

Cleanliness of certain preparation areas or rooms is becoming a bigger issue for a diverse group of organizations such as pharmaceutical and medical device manufacturers, industrial research facilities, patient care facilities, animal research facilities, and electronics laboratories. Clean facilities also help to ensure the integrity of research, development, and manufacture by keeping potential contaminants at bay.

Cleanliness is an issue particularly in the wet environments of microelectronics laboratories. Bacteria, including *Pseudomonas putida*, can grow and flourish in such environments, leaving tools and work surfaces contaminated and unclean. Microbial infestations such as these can be eliminated using a hydrogen peroxide solution.

Methods of cleaning tools and surface areas include applying hydrogen peroxide to the surface, typically through a spray bottle, then scrubbing the surface with the wipe. Another method is applying the hydrogen peroxide to the wipe and then scrubbing the surface with the wipe. While a solution of six percent (6%) hydrogen peroxide is found to be acceptable in killing bacterial growths, the use of free liquid hydrogen peroxide poses both health and safety issues.

Hydrogen peroxide, as well as other liquid cleaning solutions can be difficult to work with. Most liquid cleaning solutions, especially hydrogen peroxide, lose their cleaning potency over time because the cleaning agents are constantly decomposing. For example, hydrogen peroxide decomposes to water and oxygen over time, such that once prepared, the shelf life is extremely short. Furthermore, typically hydrogen peroxide is in a concentrated form of approximately thirty-one percent (31%) and needs to be diluted to a usable concentration such as six percent (6%) just before use. Improper measuring/proportions of the hydrogen peroxide and the solvent, typically water, however, can cause excessive dilution of the hydrogen peroxide, decreasing the effectiveness of the resulting solution.

Further, when liquid cleaning solutions are used, there is often too little solution used, leaving an unsanitized environment; and, in other cases, there is too much solution used, resulting in solution wastage. Moreover, the dilutions of some cleaning solutions may be too weak to be effective, liquid cleaning solution may be spilled, and juggling two or more containers for measuring and diluting the cleaning solution can all be time-consuming, inconvenient, unsafe, and inefficient.

To alleviate some of these problems, wipes that are pre-wetted with an appropriate amount of cleaning solution and then packaged, have been used. A problem with these wipes, however, is that, in addition to the cleaning solution losing its strength or potency over time if not used soon after packaging, the solution reacts with most common fabrics used for the wipes. The reaction causes degradation of the wiping material and of the cleaning agents within a short period of time.

As provided in U.S. Pat. Nos. 6,062,381 and 6,001,187, Paley and others addressed the wipe degradation issue. These patents disclose a small container storing an appropriate amount of cleaning solution positioned within a larger container enclosing wipes. When the wipes are needed for cleaning purposes, the smaller container is broken, releasing the liquid onto the wipes. Because the cleaning solution and the wipes are isolated, there is reduced, if any, wipe degradation. But the problem still remains where the liquid cleaning solution loses its potency over time.

In addition, particularly with hydrogen peroxide, hydrogen peroxide continually deteriorates and produces oxygen gas such that if one attempted to package wipes pre-wetted with hydrogen peroxide solution, the gas would build up within the packaging and rupture the packaging over time. The shelf-life of such a product would be extremely short.

As a result, there still exists a need for a hydrogen peroxide point of use wetted wiper system with a long shelf life and little wiper decomposition. In addition, there is a need for an easy to use wiper system where no measuring of hydrogen peroxide is necessary and where the strength/potency of the cleaning solution is retained.

BRIEF SUMMARY OF THE INVENTION

The present invention pertains to a hydrogen peroxide point of use wetted wiper system wherein the wipers have sufficient potency at the point of use to adequately clean areas.

In an embodiment of the hydrogen peroxide point of use wiper system, a measured amount of dry urea hydrogen peroxide ($CO(NH_2)_2 \cdot H_2O_2$) (such as in crystal or tablet form), is positioned within a second compartment and isolated from a solvent, preferably 0.5% by weight hydrogen peroxide, positioned within a first compartment, by a first openable barrier. The first and second compartments are linearly aligned and at point of use can merge to combine the urea hydrogen peroxide and the 0.5% hydrogen peroxide solvent to produce a six percent (6%) by weight hydrogen peroxide solution. A third compartment with wipes, preferably formed from polyester, and more preferably knit polyester, is positioned therein and used in conjunction with the six percent (6%) hydrogen peroxide solution. The packaging is labeled with the contents of each compartment, relevant warnings, and directions for use. Frangible regions such as tear notches are present to separate the first and second compartments from the wiper compartment after wetting the wipers with the hydrogen peroxide solution.

The wipes are isolated from the dry urea hydrogen peroxide solid and 0.5% hydrogen peroxide liquid by second and first openable barriers. After the first openable barrier is opened to form the six percent (6%) hydrogen peroxide solution, the second openable barrier is opened, allowing the newly formed six percent (6%) hydrogen peroxide solution to wet the wipes. The wipes may then be used to clean an area.

The first openable barrier is a seal, which, when opened, allows the solvent and the urea hydrogen peroxide to mix to form the cleaning solution. Preferably, the first openable barrier is opened around the time that the hydrogen peroxide solution will be used to clean an area, at the point of use. Because six percent (6%) hydrogen peroxide solution is only formed after combining the dry urea hydrogen peroxide with the solvent, 0.5% hydrogen peroxide, and because the solution will be used shortly after it is formed, problems of deteriorating cleaning agents are alleviated. In addition, because the wipers would be saturated with the cleaning agent only shortly prior to cleaning, the wipes will not deteriorate/disintegrate. Moreover, gas production associated with hydrogen peroxide degradation does not become an issue with point of use wipers.

These and other features and advantages of the present invention will be apparent from the following detailed description, in conjunction with the appended claims.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying drawings, wherein.

DETAILED DESCRIPTION OF THE INVENTION

Figure 1:
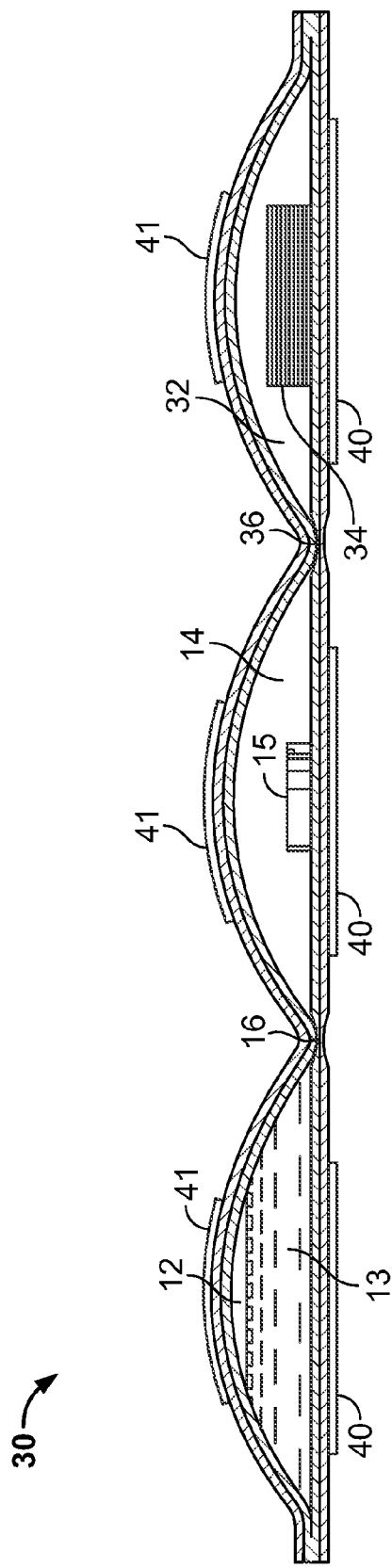
FIG. 1 is a cross-sectional view of an embodiment of the hydrogen peroxide point of use wiper system of the present invention.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

It should be further understood that the title of this section of this specification, namely, "Detailed Description Of The Invention", relates to a requirement of the United States Patent Office, and does not imply, nor should be inferred to limit the subject matter disclosed herein.

The hydrogen peroxide point-of-use wipes of the present invention pertain to providing a hydrogen peroxide point of use wetted wipe with sufficient strength or potency at time of use to clean an environment. In one embodiment, a solvent, a 0.5% by weight hydrogen peroxide solution, made with de-ionized water, is positioned within a first compartment and isolated from dry, urea hydrogen peroxide, the urea hydrogen peroxide ($CO(NH_2)_2 \cdot H_2O_2$), positioned in a second compartment. The urea hydrogen peroxide and solvent are isolated by an openable barrier, which can be opened when the cleaning solution is needed, e.g., at the point of use. When needed, the barrier is opened, and the 0.5% hydrogen peroxide solvent and the urea hydrogen peroxide solid combine to produce six percent (6%) by weight hydrogen peroxide cleaning solution.

Wipes are positioned within a third compartment and are isolated from the urea hydrogen peroxide and the solvent by first and second openable barriers. When wipes are needed to clean an area, after the cleaning solution is formed by opening the first barrier, the second barrier is opened and the cleaning solution, the hydrogen peroxide, wets the wipes. The available hydrogen peroxide solution for wetting the wipers is pre-determined based on the size, material, and number of wipers enclosed. The wipes are then ready for cleaning surfaces within an area. Frangible regions such as tear notches on the packaging allow the first and second compartments to be separated from the third compartment after the solution is mixed and the wipers are wet. Labels on the packaging indicate compartment contents, directions for use, and/or pertinent warnings.

The hydrogen peroxide point of use wiper system can be stored for extended periods and still provide liquid hydrogen peroxide of sufficient strength and potency because its solid form, urea hydrogen peroxide, does not decompose as readily as liquid hydrogen peroxide. It will be appreciated that sufficient strength or potency means that a sufficiently high concentration of the "cleaning agent" of the formulation is present, such that the solution falls within the acceptable standards.

Figure 2:
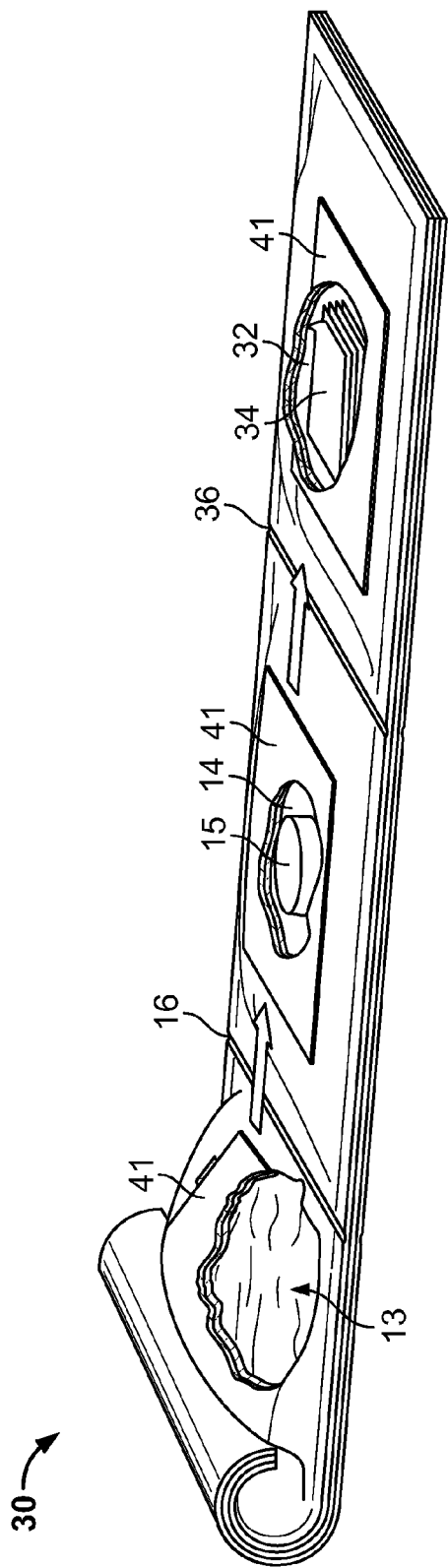
FIG. 2 is a perspective view of the system of FIG. 1.

An embodiment of the hydrogen peroxide point of use wiper system 30, shown in FIGS. 1 and 2, includes first and second compartments 12, 14 separated by a first openable barrier 16. The solvent 13 is positioned within the first compartment 12 and is isolated from the urea hydrogen peroxide 15, which is positioned within the second compartment 14. Labels 40, 41 are positioned on the top and/or bottom of the packaging to indicate compartment contents, directions for use, and/or pertinent warnings. FIG. 1 shows labels 40, 41 located on both the top and bottom of the packaging, on each compartment; however, it is anticipated that the labels may be placed on just the top, just the bottom, on one or more compartments, or in any combination thereof.

The first openable barrier 16 separating the solvent 13 from the urea hydrogen peroxide 15 positioned within the first and second compartments 12, 14 should be strong enough to prevent unintentional opening, but be readily openable so that, when the cleaning solution is needed, the first openable barrier 16 may be opened by individuals of varying strengths.

The third compartment 32 includes wipes 34, preferably polyester and more preferably knit polyester wipers, that are isolated from the urea hydrogen peroxide 15 and solvent 13 of the first and second compartments 12, 14 by a second openable barrier 36 and the first openable barrier 16.

The second openable barrier 36 is preferably opened a predetermined time after the first openable barrier 16 is opened, during which time the urea hydrogen peroxide 15 and solvent 13 mix to form the cleaning solution, hydrogen peroxide. After the hydrogen peroxide solution is formed and the second openable barrier 36 is opened, the hydrogen peroxide solution enters into the third compartment 32 and saturates the wipes 34.

The first embodiment may also include other configurations not shown, such as vertical configurations where the first compartment is positioned above (or below) the second compartment. In a vertical configuration, the openable barrier can be between the first and second compartments. For example, the barrier may be below the first compartment if the first compartment is above the second compartment. The type, positioning and strength of the first openable barrier may be adjusted based on various factors, such as the configuration of the compartments, the maximum strength seal that may be used based on the individuals who will be opening the first openable barrier and the like.

As shown in FIG. 2, the urea hydrogen peroxide 15 is positioned adjacent to the second openable barrier 36. The urea hydrogen peroxide 15 can be provided in a dry form, such as in a crystal or tablet form.

Those of skill in the art will appreciate that in addition to the three compartment linear configuration shown in FIGS. 1, 2 other configurations of the invention are possible. Such configurations include, for example, vertical alignment of the compartments, or configurations in which one of the compartments is positioned within the other compartment or all of the compartments are positioned within a larger compartment.

Moreover, for added cleanliness, safety, and spill control, it will be appreciated that the compartments may be double-bagged.

By forming the hydrogen peroxide cleaning solution using the point of use wiper system of the invention, the cleaning solution is more potent when actually used as opposed to using a prepared cleaning solution that has been waiting in storage.

In a preferred embodiment, the newly formed cleaning solution is utilized within twenty-four hours after it has been formed. In other embodiments, depending on the desired cleaning agent potency, the newly formed cleaning solution may be utilized within a shorter or after a longer time than the twenty-four hour period of the preferred embodiment.

In some embodiments, the urea hydrogen peroxide 15 may include other ingredients. For example, when used in tablet form, the urea hydrogen peroxide 15 may include effervescing agents for reacting with water to form carbon dioxide to break up the tablet. The urea hydrogen peroxide 15 may also include neutralizing agents to maintain the pH of the cleaning solution after it is formed. In some embodiments, the urea hydrogen peroxide 15 may also include the active cleaning agent for which various organizations, such as the U.S. federal government, provide concentration guidelines.

The solvent 13 is preferably a 0.5% solution of hydrogen peroxide and water and, depending on purity tolerances, may be made with tap water, deionized water, or distilled water.

Preferably, the wipes 34 are polyester and more preferably knit polyester. The wipes may be formed from other suitable, compatible materials such as polypropylene or the like.

When using the hydrogen peroxide wetted wipers 30, the certain amounts and concentrations of urea hydrogen peroxide 15 and 0.5% hydrogen peroxide solvent 13 were found to form a cleaning solution to adequately saturate the wipes. The amount of urea hydrogen peroxide 15 and solvent 13 is to be determined by the wiper 34 absorptive capacity, number, size, and the degree of desired saturation.

All patents referred to herein, are hereby incorporated herein by reference, whether or not specifically do so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be made to the invention without departing from the true spirit and scope of the novel concepts of the present invention. It is to be understood that no limitation with respect to the specific embodiments illustrated is intended or to be inferred. The disclosure is intended to cover all such modifications as fall within the scope of the invention.

What is claimed is:

1. A hydrogen peroxide point of use wetted wiper system comprising:
a packaging with a first compartment, a second compartment, and a third compartment, wherein the compartments are mergable and separable, the packaging having frangible regions for separating each compartment from its adjacent compartments;
at least one wiper, wherein the at least one wiper is disposed in the third compartment;
a cleaning solid, wherein the cleaning solid is urea hydrogen peroxide, and wherein the urea hydrogen peroxide is disposed in the second compartment, isolated from the at least one wiper; and
a solvent, the solvent being 0.5% hydrogen peroxide by weight, wherein the solvent is disposed in the first compartment, and wherein the solvent is isolated from the at least one wiper and the urea hydrogen peroxide, and wherein the first and second compartments are merged to form a unified compartment such that the solvent is combined with the urea hydrogen peroxide at a point of use to form a liquid hydrogen peroxide that is a 6% by weight hydrogen peroxide solution, and wherein the unified compartment is merged with the third compartment such that the liquid hydrogen peroxide wets the at least one wiper, the liquid hydrogen peroxide concentration and amount proportional to the wiper absorptive capacity, size, and degree of desired saturation,
wherein the packaging is labeled.

2. The hydrogen peroxide point of use wetted wiper system in accordance with claim 1 wherein the solvent is formed from deionized water.

3. The hydrogen peroxide point of use wetted wiper system in accordance with claim 1 wherein the solvent is formed from distilled water.

4. The hydrogen peroxide point of use wetted wiper system in accordance with claim 1 wherein the packaging is double-bagged.

5. The hydrogen peroxide point of use wetted wiper system in accordance with claim 1 wherein the wipers are formed from polyester.

6. The hydrogen peroxide point of use wetted wiper system in accordance with claim 1 wherein the wipers are a polyester/cellulose blend.

7. The hydrogen peroxide point of use wetted wiper system in accordance with claim 1 wherein the wipers are cotton.

8. The hydrogen peroxide point of use wiper system in accordance with claim 1 wherein the wipers are rayon.

9. The hydrogen peroxide point of use wetted wiper system in accordance with claim 5 wherein the wipers are a knit polyester.

* * * * *